United States Patent [19]

Hagermann et al.

[11] Patent Number: 5,780,214
[45] Date of Patent: Jul. 14, 1998

[54] COLOR PHOTOGRAPHIC SILVER HALIDE MATERIAL WITH TIO$_2$ AND U.V. ABSORBER

[75] Inventors: Jörg Hagermann, Köln; Arno Schmuck, Leichlingen, both of Germany

[73] Assignee: Agfa-Gevaert AG, Germany

[21] Appl. No.: 853,514

[22] Filed: May 9, 1997

[30] Foreign Application Priority Data

May 17, 1996 [DE] Germany ............... 196 19 946.8

[51] Int. Cl.$^6$ .................................................. G03C 1/815
[52] U.S. Cl. ................................... 430/512; 430/931
[58] Field of Search ............................... 430/512, 931

[56] References Cited

U.S. PATENT DOCUMENTS

| | | | |
|---|---|---|---|
| 3,833,380 | 9/1974 | Crawford et al. | 430/931 |
| 4,563,406 | 1/1986 | Ohbayashi et al. | 430/513 |
| 5,075,206 | 12/1991 | Noda et al. | 430/531 |
| 5,462,846 | 10/1995 | Yaneyama | 430/512 |
| 5,674,668 | 10/1997 | Hagemann et al. | 430/512 |

FOREIGN PATENT DOCUMENTS

| | | |
|---|---|---|
| 9454833 | 8/1994 | Australia. |
| 0 609 533 | 8/1994 | European Pat. Off.. |
| 19511316 | 2/1996 | Germany. |

OTHER PUBLICATIONS

Industrial Inorganic Pigments, Gunter Buxbaum, Weinheim, N.Y., pp. 227–228.

Orbit Abstract of EP 0 609 533 (Aug. 10, 1994) and AU 9454833 (Aug. 4, 1994).

*Primary Examiner*—Richard L. Schilling
*Attorney, Agent, or Firm*—Connolly & Hutz

[57] ABSTRACT

The light stability of a color photographic silver halide material is improved if, as UV protection, a) a TiO$_2$ pigment having a primary particle diameter of 1 to 100 nm is added to one layer and b) a hydroxyphenylbenzotriazole compound and/or a hydroxyphenyltriazine compound is added to the same or a different layer of the material.

9 Claims, No Drawings

COLOR PHOTOGRAPHIC SILVER HALIDE MATERIAL WITH TIO₂ AND U.V. ABSORBER

Colour photographic materials always contain UV absorbers in order to improve or maintain the light stability of the image dyes present in the material after processing. High UV daylight can bleach the image dyes.

The compounds conventionally used in photographic materials to absorb UV light are, for example, aryl-substituted benzotriazole compounds (U.S. Pat. No. 3,533,794, DE 42 29 233), 4-thiazolidone compounds (U.S. Pat. No. 3,314,794, U.S. Pat. No. 3,352,681), benzophenone compounds (JP-A-2784/71), cinnamic acid esters (U.S. Pat. No. 3,705,805, U.S. Pat. No. 3,707,375), butadiene compounds (U.S. Pat. No. 4,045,229), benzoxazole compounds (U.S. Pat. No. 3,700,455), aryl-substituted triazine compounds (DE 21 13 833, EP 520 938, EP 530 135, EP 531 258) and benzoylthiophene compounds (GB 973 919, EP 521 823). UV absorbing couplers or polymers, which may be immobilised in a specific layer by mordanting, are also used.

One disadvantage of these organic compounds is that they are themselves light stable only to a limited extent. Once the UV absorbing compounds have been destroyed by light, the image dyes begin to bleach more markedly.

This disadvantage may be overcome by using $TiO_2$ pigments having an average primary particle diameter of 1 to 100 nm, preferably of 5 to 50 nm. These $TiO_2$ pigments are transparent and, unlike conventional $TiO_2$-based white pigments (rutile and anatase) with an optimum particle size of approximately 0.2 μm, they have virtually no light-scattering characteristics. They are moreover colourless. Transparent $TiO_2$ in rutile form is particularly advantageous as a UV absorber for photographic material.

Particularly advantageous $TiO_2$ pigments are those in which more than 90% of the primary particles have a diameter of less than 100 nm.

Transparent $TiO_2$ pigments having the stated characteristics are known, for example, from Gunter Buxbaum, *Industrial Inorganic Pigments*, VCH Weinheim, New York, Basel, Cambridge, Tokyo (1993), pages 227 to 228.

It is known from DE 43 02 896 that $TiO_2$ pigments containing iron oxide have an overall higher absorbance in the UV range than corresponding $TiO_2$ pigments containing no iron oxide.

$Fe_2O_3$ may primarily be considered as the iron oxide. $TiO_2$ of rutile structure is preferably used.

The $TiO_2$ pigments containing iron oxide according to the invention are preferably coated on the surface with $SiO_2$ or $Al_2O_3$.

The $TiO_2$ pigments optionally containing iron oxide exhibit only slight absorption in the important range between 320 and 400 nm.

SUMMARY OF THE INVENTION

An object of the invention is to provide UV absorbers for photographic materials which impart elevated light stability to the materials.

It has now been found that this object may be achieved by the combined use of organic compounds of the following formula (I) and/or (II), on the one hand, and $TiO_2$ pigments having an average primary particle diameter of 1 to 100 nm, on the other hand:

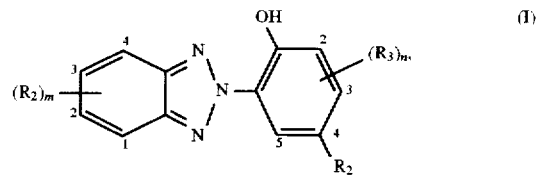

in which $R_1$, $R_3$ means halogen, alkyl, alkoxy, aryloxy, alkylthio, arylthio, acyloxy, acylamino or acyl;

$R_2$ means alkyl or acyl and m, n mean 0, 1 or 2 and two or more residues $R_1$, $R_3$ are identical or different

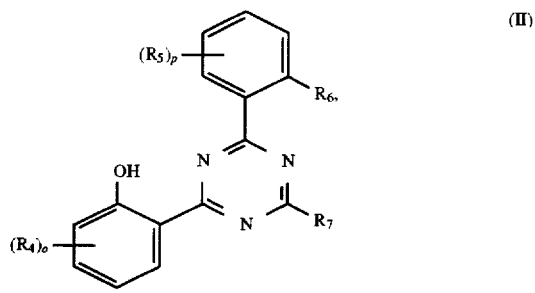

in which $R_4$ and $R_5$ mean H, halogen, hydroxy, mercapto, alkyl, aryl, alkoxy, aryloxy, acyloxy, alkylthio, arylthio, —$NR_8$—$R_9$, alkoxycarbonyl, carbamoyl or sulphamoyl;

$R_6$ means H, hydroxy, halogen or alkyl;

$R_7$ means alkyl, alkoxy, alkylthio, aryloxy, arylthio or a residue of the formula

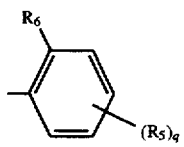

$R_8$ means H, alkyl or aryl;

$R_9$ means H, alkyl, aryl, acyl, alkoxycarbonyl, carbamoyl, sulphamoyl or sulphonyl;

o, p and q (identical or different) mean 1, 2, 3 or 4, and in which two or more residues $R_4$, $R_5$ and $R_6$ are identical or different.

DETAILED DESCRIPTION OF THE INVENTION

The alkyl and aryl groups of the formulae I and II may be further substituted, for example by OH, halogen, COOH, $SO_3H$, acyl, acylamino, acyloxy, alkoxy, aryloxy, alkylthio, arylthio, alkylsulphonyl, arylsulphonyl, alkyl and aryl.

Acyl residues may be derived from aliphatic or aromatic carboxylic, carbonic, carbamic, sulphonic, sulphinic, phosphoric, phosphonic or phosphinic acids.

Examples of compounds of the formula (I) are:

| Example No. | $R_1$ | $R_2$ | $R_3$ |
|---|---|---|---|
| I-1 | H | t-$C_4H_9$ | 2-s-$C_4H_9$ |
| I-2 | H | t-$C_5H_{11}$ | 2-t-$C_5H_{11}$ |
| I-3 | H | $CH_3$ | 2-i-$C_{12}H_{25}$ |
| I-4 | 2-$OC_2H_5$ | t-$C_4H_9$ | 2-t-$C_4H_9$ |
| I-5 | 2-Cl | $-(CH_2)_2-CO_2$-i-$C_8H_{17}$ | 2-t-$C_4H_9$ |
| I-6 | H | t-$C_4H_9$ | H |
| I-7 | 2-$SC_8H_{17}$-i | $CH_3$ | 2-t-$C_4H_9$ |
| I-8 | 2-$OC_3H_7$-i; 3-$OC_3H_7$-i | s-$C_4H_9$ | 2-s-$C_4H_9$ |
| I-9 | 2,3-O−$CH_2$−O− | $CH_3$ | 2-t-$C_4H_9$ |
| I-10 | H | $C_{12}H_{25}$ | H |
| I-11 | H | t-$C_8H_{17}$ | H |
| I-12 | 2-Cl | t-$C_4H_9$ | 2-t-$C_4H_9$ |
| I-13 | H | t-$C_4H_9$ | t-$C_4H_9$ |
| I-14 | 2-Cl | $CH_3$ | 2-t-$C_4H_9$ |
| I-15 | H | $(CH_2)_2CO_2C_8H_{17}$-i | 2-t-$C_4H_9$ |
| I-16 | H | $-C(CH_3)_2$-phenyl | 2-$C(CH_3)_2$-phenyl |

I-17 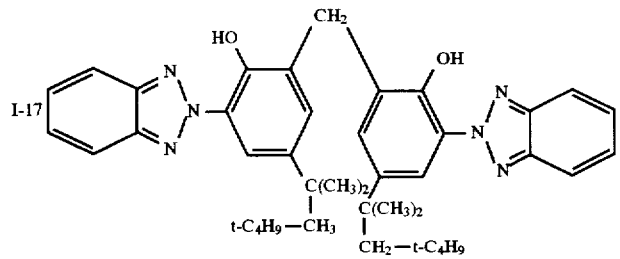

In a preferred embodiment of the invention, the compounds of the formula (II) are of the formula (III)

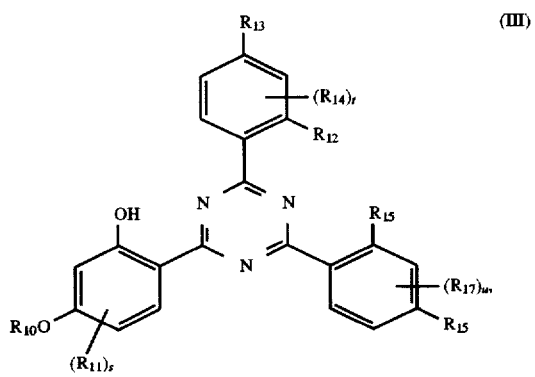

(III)

in which $R_{10}$ means H, alkyl, aryl or acyl;

$R_{11}$, $R_{14}$ and $R_{17}$ mean halogen, alkyl, aryl, alkoxy, aryloxy, acyloxy, alkylthio, arylthio or acylamino;

$R_{12}$, $R_{13}$, $R_{15}$ and $R_{16}$ (identical or different) mean H, −OH or $R_{11}$;

s, t and u mean 0, 1 or 2.

An alkyl residue represented by $R_{10}$ to $R_7$ or contained therein may be linear, branched or cyclic and contain 1–36, preferably 1–20, C atoms. An alkyl or aryl residue represented by $R_{10}$ to $R_{17}$ or contained therein may itself be substituted; possible substituents are the groups stated for $R_{11}$. An acyl residue represented by $R_{10}$ to $R_{17}$ or contained therein may be derived from an aliphatic or aromatic carboxylic or sulphonic acid, a carbonic acid semi-ester, a carbamic acid or sulphonamide, a phosphoric or phosphonic acid. Two or more residues $R_{11}$, $R_{14}$ and $R_{17}$ may be identical or different; these residues preferably denote alkyl, aryl, acylamino, acyloxy, halogen and/or alkoxy.

The following are examples of compounds of the formula (II) preferred according to the invention (IV)

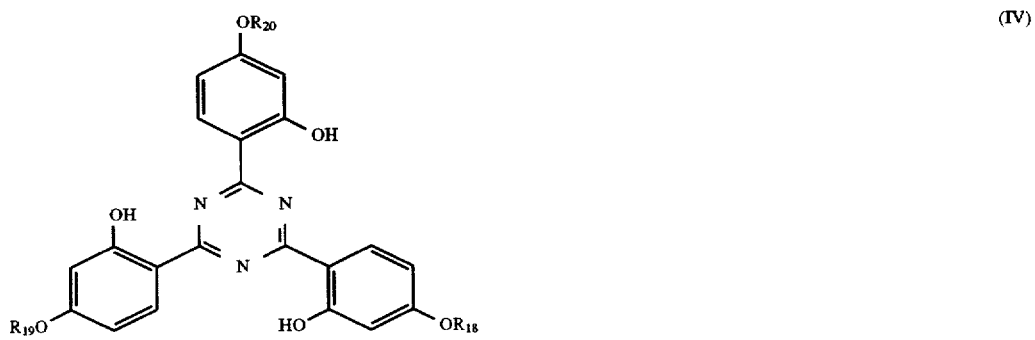

II-1   $R_{18} = R_{19} = R_{20} = -CH_2-CH(OH)-CH_2-O-C_8H_{17}\text{-}i$

II-2   $R_{18} = R_{19} = R_{20} = -CH_2-CH(OH)-C_6H_{13}$

II-3   $R_{18} = R_{19} = -C_4H_9\text{-s}, R_{20} = -C_{13}H_{25}\text{-}i$

II-4   $R_{18} = -CH_2-CH(OH)-CH_2-O-C_4H_9\text{-s}$
$R_{19} = -CH_2-CH(OH)-CH_2-O-CH(CH_3)(C_3H_7)$
$R_{20} = R_{18}, R_{19} (1:1)$ II-5   $R_{18} = -CH_2-CH_2-O-CH_2-CH_2-O-C_4H_9, R_{19} = R_{20} = -CH_2-CO_2-C_8H_{17}\text{-}i,$ II-6   $R_{18} = R_{19} = R_{20} = -CH_2-CH(CH)-CH_2-O-CH_2-CH_2-O-CH(CH_3)(C_2H_5)$ (V)

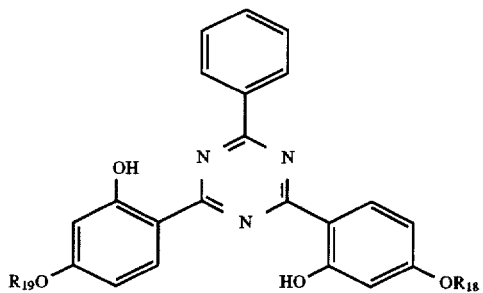

II-7   $R_{18} = R_{19} = -CH_2-CH(OH)-CH_2-O-C_9H_{19}\text{-}i$

II-8   $R_{18} = CH_2-CO-C_4H_9\text{-}i, R_{19} = -CH_2-CO_2-C_{13}H_{20}\text{-}i,$

II-9   $R_{18} = R_{19} = -(CH_2-CH_2-O)_4-CH_3,$

II-10   $R_{18} = R_{19} = -C_{10}H_{21}\text{-}i$

II-11   $R_{18} = -CH_2-CH(OH)-CH_2-O-C_4H_9\text{-s}$
$R_{19} = -CH_2-CH(OH)-CH_2-O-C(CH_3)(C_3H_7)$

II-12

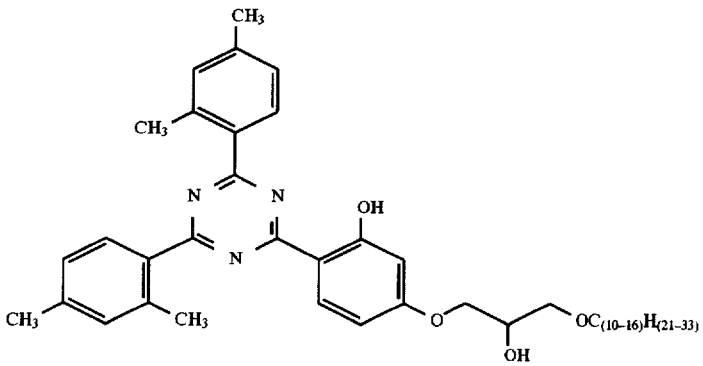

II-13
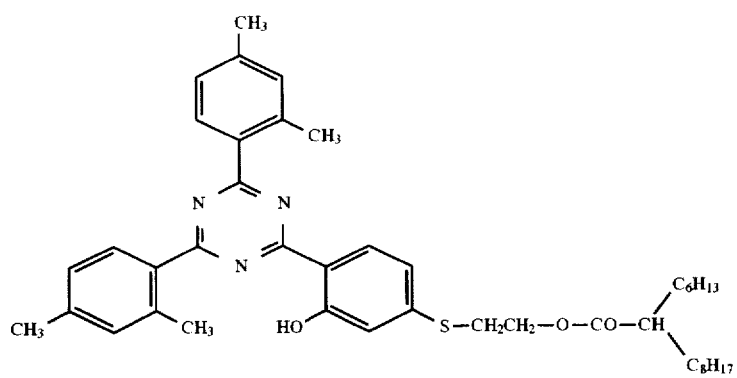
II-14
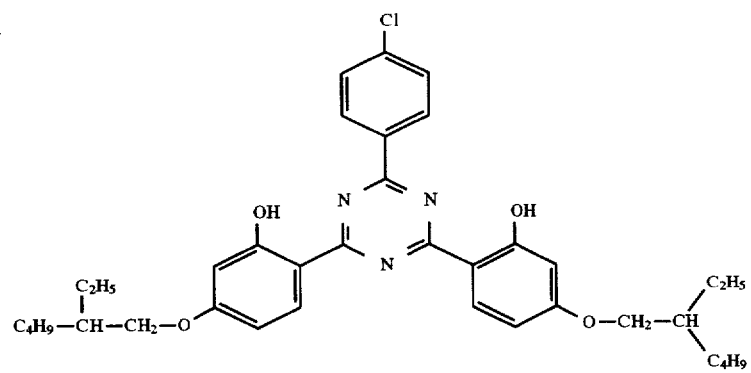
II-15
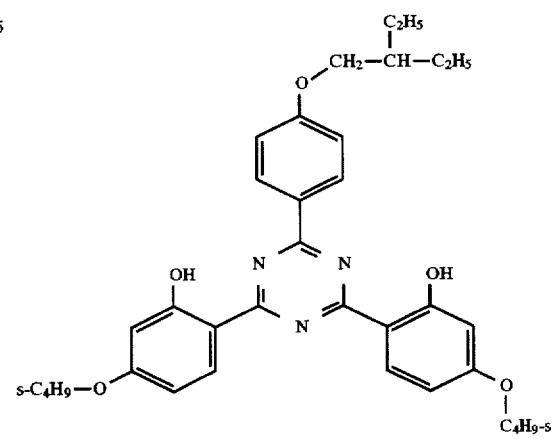
II-16
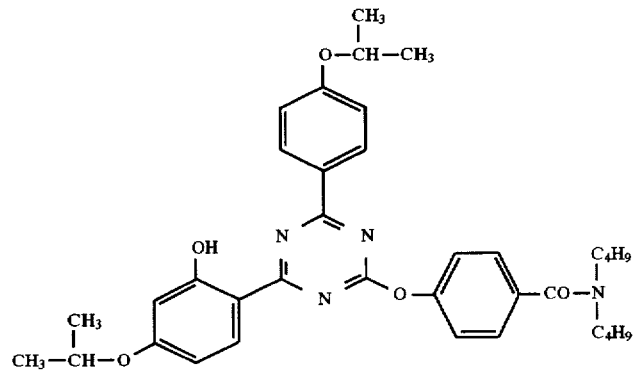

II-17
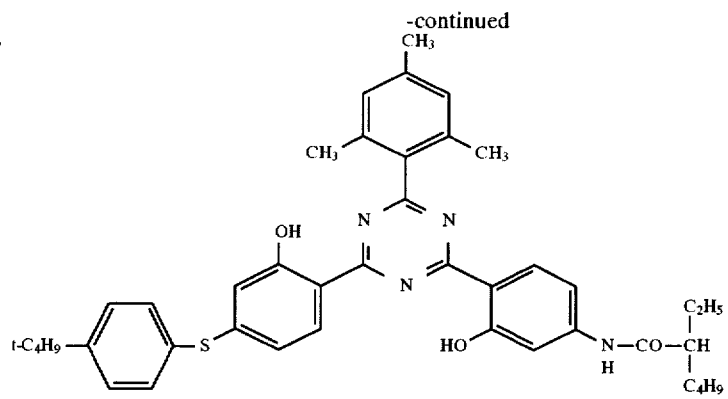

II-18
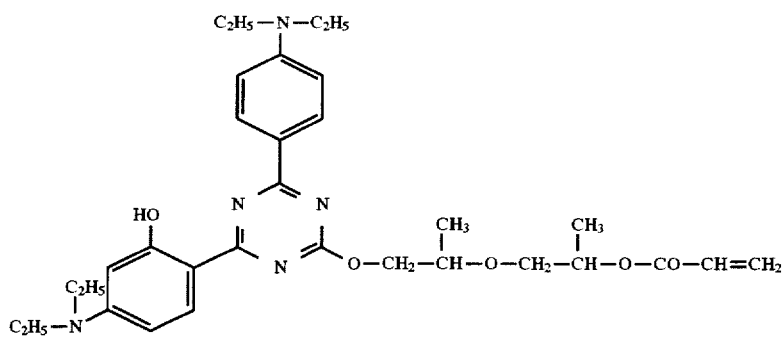

II-19
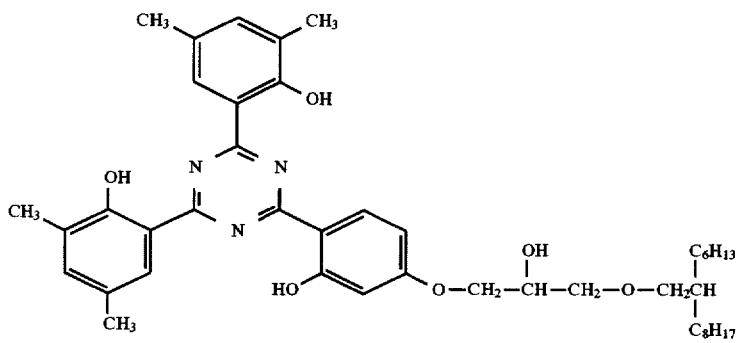

II-20
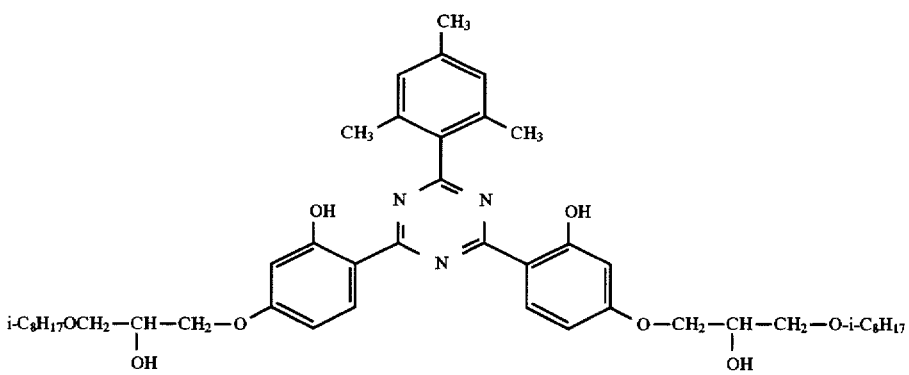

The $TiO_2$ pigments according to the invention and the compounds of the formulae (I) and/or (II) are located either in a layer in which the dye to be protected against UV light is produced or in a layer which is arranged closer to the light source than the above-stated layer or they are distributed through the layers.

The $TiO_2$ pigment is used in a total quantity of 5 to 3000 mg/m², preferably of 50 to 2000 mg/m², the compounds of the formulae (I) and (II) are used in a total quantity of 10 to 2000 mg/m², preferably of 20 to 1000 mg/m².

The $TiO_2$ pigment may contain up to 20 wt. % of $Fe_2O_3$, relative to the sum of $TiO_2$ and $Fe_2O_3$, and be coated with $SiO_2$ or $Al_2O_3$, wherein 1 to 5 wt. % of $SiO_2$ or $Al_2O_3$, relative to the sum of $TiO_2$ and $Fe_2O_3$, are advantageously used.

The $TiO_2$ pigments are preferably dispersed in gelatine; the compounds of the formulae (I) and (II) are preferably dispersed or emulsified in gelatine, optionally together with a high boiling solvent.

Suitable TiO$_2$ pigments are:

P-A: TiO$_2$, rutile modification, primary particle size 30 nm

P-B: TiO$_2$ with 2 wt. % Fe$_2$O$_3$ (relative to TiO$_2$+Fe$_2$O$_3$), rutile modification, primary particle size 25 nm P-C: TiO$_2$ with 3 wt. % Fe$_2$O$_3$ (relative to TiO$_2$+Fe$_2$O$_3$), anatase modification, primary particle size 30 nm All pigments are coated with 3 wt. % of Al$_2$O$_3$, relative to TiO$_2$+Fe$_2$O$_3$.

Examples of colour photographic materials are colour negative films, colour reversal films, colour positive films, colour photographic paper, colour reversal photographic paper, colour-sensitive materials for the dye diffusion transfer process or the silver dye bleaching process.

The photographic materials consist of a support onto which at least one photosensitive silver halide emulsion layer is applied. Thin films and sheets are in particular suitable as supports. A review of support materials and the auxiliary layers applied to the front and reverse sides of which is given in Research Disclosure 37254, part 1 (1995), page 285.

The TiO$_2$ pigments containing iron oxide according to the invention are preferably added to colour photographic print materials, i.e. colour photographic paper and transparent colour photographic film for display purposes.

The colour photographic materials conventionally contain at least one red-sensitive, one green-sensitive and one blue-sensitive silver halide emulsion layer, optionally together with interlayers and protective layers.

Depending upon the type of the photographic material, these layers may be differently arranged. This is demonstrated for the most important products:

Colour photographic films such as colour negative films and colour reversal films have on the support, in the stated sequence, 2 or 3 red-sensitive, cyan-coupling silver halide emulsion layers, 2 or 3 green-sensitive, magenta-coupling silver halide emulsion layers and 2 or 3 blue-sensitive, yellow-coupling silver halide emulsion layers. The layers of identical spectral sensitivity differ with regard to their photographic sensitivity, wherein the less sensitive partial layers are generally arranged closer to the support than the more highly sensitive partial layers.

A yellow filter layer is conventionally located between the green-sensitive and blue-sensitive layers which prevents blue light from reaching the underlying layers.

Possible options for different layer arrangements and the effects thereof on photographic properties are described in *J. Inf. Rec. Mats.*, 1994, volume 22, pages 183–193.

Colour photographic paper, which is usually substantially less photosensitive than a colour photographic film, conventionally has on the support, in the stated sequence, one blue-sensitive, yellow-coupling silver halide emulsion layer, one green-sensitive, magenta-coupling silver halide emulsion layer and one red-sensitive, cyan-coupling silver halide emulsion layer; the yellow filter layer may be omitted.

The number and arrangement of the photosensitive layers may be varied in order to achieve specific results. For example, all high sensitivity layers may be grouped together in one package of layers and all low sensitivity layers may be grouped together in another package of layers in order to increase sensitivity (DE 25 30 645).

The substantial constituents of the photographic emulsion layers are binder, silver halide grains and colour couplers.

Details of suitable binders may be found in *Research Disclosure* 37254, part 2 (1995), page 286.

Details of suitable silver halide emulsions, the production, ripening, stabilisation and spectral sensitisation thereof, including suitable spectral sensitisers, may be found in *Research Disclosure* 37254, part 3 (1995), page 286 and in *Research Disclosure* 37038, part XV (1995), page 89.

Photographic materials with camera sensitivity conventionally contain silver bromide-iodide emulsions, which may optionally also contain small proportions of silver chloride. Photographic print materials contain either silver chloride-bromide emulsions with up to 80 mol. % of AgBr or silver chloride-bromide emulsions with above 95 mol. % of AgCl.

Details relating to colour couplers may be found in *Research Disclosure* 37254, part 4 (1995), page 288 and in *Research Disclosure* 37038, part II (1995), page 80. The maximum absorption of the dyes formed from the couplers and the developer oxidation product is preferably within the following ranges: yellow coupler 430 to 460 nm, magenta coupler 540 to 560 nm, cyan coupler 630 to 700 nm.

In order to improve sensitivity, grain, sharpness and colour separation in colour photographic films, compounds are frequently used which, on reaction with the developer oxidation product, release photographically active compounds, for example DIR couplers which eliminate a development inhibitor.

Details relating to such compounds, in particular couplers, may be found in *Research Disclosure* 37254, part 5 (1995), page 290 and in *Research Disclosure* 37038, part XIV (1995), page 86.

Colour couplers, which are usually hydrophobic, as well as other hydrophobic constituents of the layers, are conventionally dissolved or dispersed in high-boiling organic solvents. These solutions or dispersions are then emulsified into an aqueous binder solution (conventionally a gelatine solution) and, once the layers have dried, are present as fine droplets (0.05 to 0.8 μm in diameter) in the layers.

Suitable high-boiling organic solvents, methods for the introduction thereof into the layers of a photographic material and further methods for introducing chemical compounds into photographic layers may be found in *Research Disclosure* 37254, part 6 (1995), page 292.

The non-photosensitive interlayers generally located between layers of different spectral sensitivity may contain agents which prevent an undesirable diffusion of developer oxidation products from one photosensitive layer into another photosensitive layer with a different spectral sensitisation.

Suitable compounds (white couplers, scavengers or DOP scavengers) may be found in *Research Disclosure* 37254, part 7 (1995), page 292 and in *Research Disclosure* 37038, part III (1995), page 84.

The photographic material may also contain optical brighteners, spacers, filter dyes, formalin scavengers, light stabilisers, anti-oxidants, D$_{min}$ dyes, additives to improve the stability of dyes, couplers and whites and to reduce colour fogging, plasticisers (latices), biocides and others.

Suitable compounds may be found in *Research Disclosure* 37254, part 8 (1995), page 292 and in *Research Disclosure* 37038, parts IV, V, VI, VII, X, XI and XIII (1995), pages 84 et seq.

The layers of colour photographic materials are conventionally hardened, i.e. the binder used, preferably gelatine, is crosslinked by appropriate chemical methods.

Suitable hardener substances may be found in *Research Disclosure* 37254, part 9 (1995), page 294 and in *Research Disclosure* 37038, part XII (1995), page 86.

Once exposed with an image, colour photographic materials are processed using different processes depending upon their nature. Details relating to processing methods and the

EXAMPLE

Sample 1

A colour photographic recording material was produced by applying the following layers in the stated sequence onto a film support of paper coated on both sides with polyethylene. Quantities are stated per 1 m². The applied quantity of silver halide is stated as the corresponding quantity of $AgNO_3$.

1st layer (substrate layer):
0.1 g of gelatine
2nd layer (blue-sensitive layer):
Blue-sensitive silver halide emulsion (99.5 mol. % chloride, 0.5 mol. % bromide, average grain diameter 0.9 µm) prepared from 0.40 g of $AgNO_3$ with
1.25 g of gelatine
0.15 g of yellow coupler GB 1
0.35 g of yellow coupler GB 2
0.50 g of tricresyl phosphate (TCP)
0.10 g of stabiliser ST-1
0.30 mg of stabiliser ST-2
0.70 mg of sensitiser S-1
3rd layer (interlayer):
1.1 g of gelatine
0.06 g of oxform scavenger O-1
0.06 g of oxform scavenger O-2
0.12 g of TCP
4th layer (green-sensitive layer)
Green-sensitised silver halide emulsion (99.5 mol. % chloride, 0.5 mol. % bromide, average grain diameter 0.47 µm) prepared from 0.25 g of $AgNO_3$ with
0.77 g of gelatine
0.25 g of magenta coupler PP 1
0.30 g of stabiliser ST-3
0.50 mg of stabiliser ST-4
0.30 g of diisooctyl phthalate
0.20 g of isotridecanol
0.70 mg of sensitiser S-2
5th layer (UV protective layer)
1.15 g of gelatine
0.50 g of UV absorber I-1
0.10 g of UV absorber I-5
0.06 g of O-1
0.06 g of O-2
0.35 g of diisononyl adipate
6th layer (red-sensitive layer)
Red-sensitised silver halide emulsion (99.5 mol. % chloride, 0.5 mol. % bromide, average grain diameter 0.50 µm) prepared from 0.25 g of $AgNO_3$ with
1.00 g of gelatine
0.46 g of cyan coupler BG 1
0.46 g of TCP
0.60 mg of stabiliser ST-5
0.03 mg of sensitiser S-3
7th layer (UV protective layer)
0.35 g of gelatine
0.15 g of I-1
0.03 g of I-5
0.09 g of TCP
8th layer (protective layer)
0.9 g of gelatine
0.3 g of hardener H 1
0.05 g of optical brightener W-1
0.07 g of polyvinylpyrrolidone
1.2 mg of silicone oil
2.5 mg of polymethyl methacrylate spacers necessary chemicals are disclosed in *Research Disclosure* 37254, part 10 (1995), page 294 and in *Research Disclosure* 37038, parts XVI to XXIII (1995), pages 95 et seq. together with example materials.

GB1

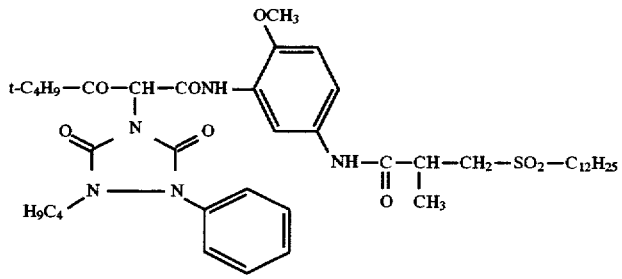

GB2

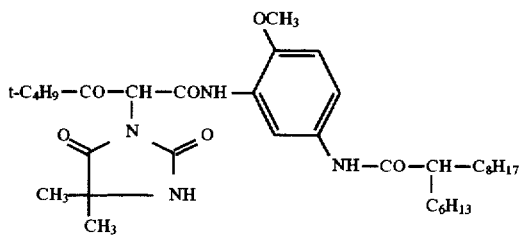

PP1

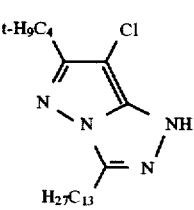

-continued
BG1
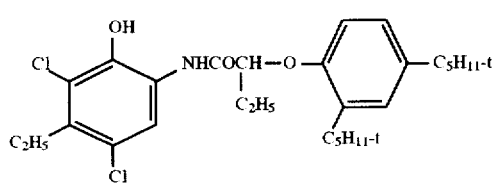
H1
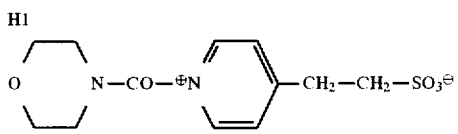
S-1
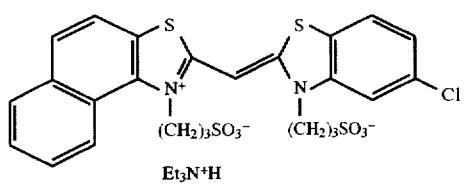
S-2
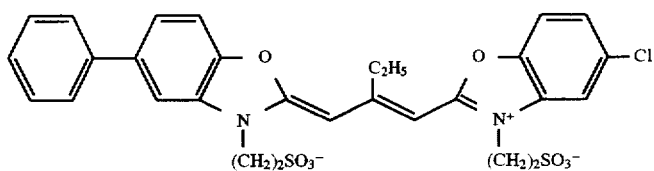
S-3
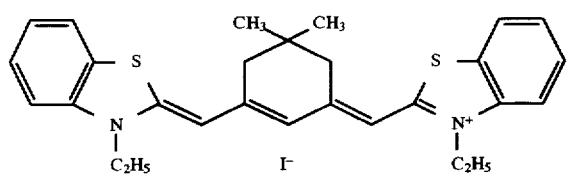
St-1: 1:1 mixtures
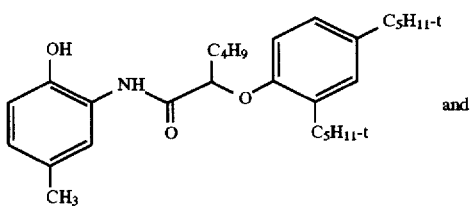 and
St-2
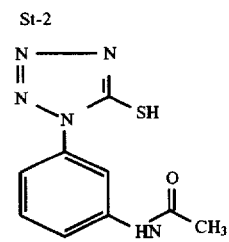
ST-3 2:1 mixture of
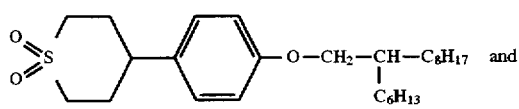 and
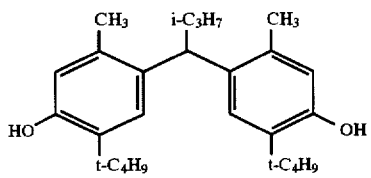
ST-4
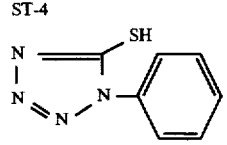
ST-5
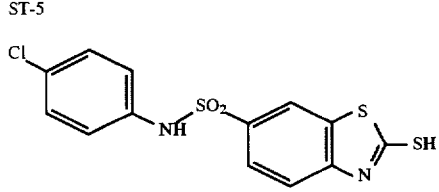

O-1
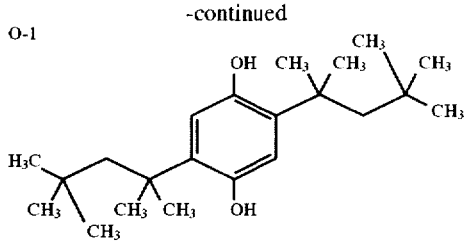

O-2
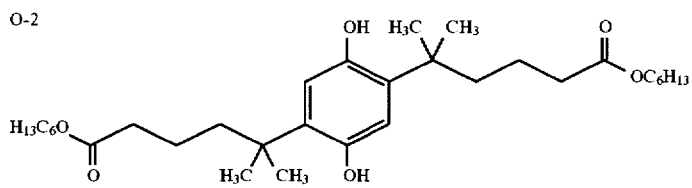

W-1
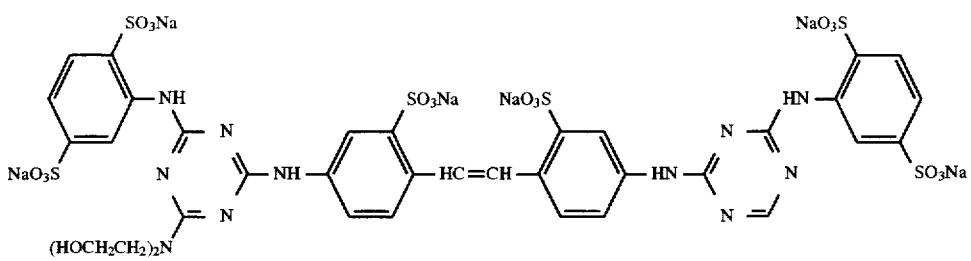

Samples 2 to 12

There are the following differences with respect to sample 1:

a) UV-I-1, UV-I-5 and 0.25 g of diisononyl adipate are omitted from the 5th layer.

b) UV-I-1, UV-I-5 and TCP are omitted from the 7th layer.

c) The quantities of compounds of the formulae (I) and (II) and of TiO$_2$ pigments stated in Table 1 are added to layers 5 to 7.

The colour photographic recording materials are exposed through a step wedge, once with a filter which transmits red light, once with a filter which transmits green light and once with a filter which transmits blue light, such that cyan, magenta and yellow colour separations are obtained. The exposed material is processed as follows:

| Stage | Time | Temperature |
|---|---|---|
| Development | 45 s | 35° C. |
| Bleach/fixing | 45 s | 35° C. |
| Rinsing | 90 s | 33° C. |

The processing baths were prepared in accordance with the following instructions:

| Colour developer solution | |
|---|---|
| Tetraethylene glycol | 20.0 g |
| N,N-diethylhydroxylamine | 4.0 g |
| (N-ethyl-N-(2-methanesulphonamido)ethyl)-4-amino-3-methyl-benzene sulphate | 5.0 g |
| Potassium sulphite | 0.2 g |
| Potassium carbonate | 30.0 g |
| Polymaleic anhydride | 2.5 g |
| Hydroxyethanediphosphonic acid | 0.2 g |
| Optical brightener (4,4'-diaminostilbene type) | 2.0 g |
| Potassium bromide | 0.02 g |
| make up to 1 l with water, adjust pH to 10.2 with KOH or H$_2$SO$_4$. | |

| Bleach/fixing bath solution | |
|---|---|
| Ammonium thiosulphate | 75.0 g |
| Sodium hydrogen sulphite | 13.5 g |
| Ethylenediaminetetraacetic acid (iron/ammonium salt) | 45.0 g |
| make up to 1 l with water, adjust pH to 6.0 with ammonia or acetic acid. | |

After processing, the colour separation (FAZ) wedges are exposed to 20 million lxh and 40 million lxh of light from a xenon lamp and the percentage changes in density at densities 0.6 and 1.4 above fog are measured.

Results: see Table 2. The Example demonstrates the overall somewhat better light stability, particularly after exposure to large quantities of light (40 million lxh), achieved when TiO$_2$ pigments are used. Stability may, however, significantly be increased with the combination according to the invention of TiO$_2$ pigments and compounds of the formulae (I) and/or (II).

TABLE 1

| Sample | Layer 5 Addition | Layer 5 Quantity [g/m²] | Layer 6 Addition | Layer 6 Quantity [g/m²] | Layer 7 Addition | Layer 7 Quantity [g/m²] |
|---|---|---|---|---|---|---|
| 1 (C) | I-1; I-5 | 0.5; 0.1 | — | — | I-1; I-5 | 0.15; 0.005 |
| 2 (C) | — | — | II-4 | 0.4 | II-12 | 0.12 |
| 3 (C) | P-A | 0.4 | — | — | P-A | 0.4 |
| 4 (C) | — | — | — | — | P-B | 0.8 |
| 5 (I) | P-A; I-2 | 0.2; 0.1 | — | — | P-A; I-14 | 0.2; 0.3 |
| 6 (I) | P-A; II-20 | 0.2; 0.2 | — | — | P-A; II-20 | 0.2; 0.2 |
| 7 (I) | — | — | — | — | P-B; II-1 | 0.35; 0.45 |
| 8 (I) | — | — | II-1 | 0.45 | P-B | 0.35 |
| 9 (I) | — | — | I-5; I-3 | 0.3; 0.1 | P-B | 0.4 |
| 10 (I) | I-3; I-14 | 0.1; 0.25 | II-11 | 0.1 | P-C | 0.35 |
| 11 (I) | P-C; II-4 | 0.35; 0.2 | I-1 | 0.25 | — | — |
| 12 (I) | P-B; I-5 | 0.2; 0.3 | P-B; I-3 | 0.2; 0.1 | — | — |

(C = comparison; I = invention)

The compounds of the formula (II) are emulsified with 50 wt. % of diisooctyl phosphate, with the exception of II-11, which is emulsified with 40 wt. % of TCP. The compound of the formula (I) are emulsified with 30 wt. % of diisononyl phthalate.

TABLE 2

| Sample no. | Yellow colour separation 20 million lxh D = 0.6 | Yellow colour separation 20 million lxh D = 1.4 | Yellow colour separation 40 million lxh D = 0.6 | Yellow colour separation 40 million lxh D = 1.4 | Magenta colour separation 20 million lxh D = 0.6 | Magenta colour separation 20 million lxh D = 1.4 | Magenta colour separation 40 million lxh D = 0.6 | Magenta colour separation 40 million lxh D = 1.4 | Cyan colour separation 20 million lxh D = 0.6 | Cyan colour separation 20 million lxh D = 1.4 | Cyan colour separation 40 million lxh D = 0.6 | Cyan colour separation 40 million lxh D = 1.4 |
|---|---|---|---|---|---|---|---|---|---|---|---|---|
| 1 (C) | −46 | −28 | −86 | −58 | −60 | −38 | −98 | −75 | −49 | −27 | −88 | −60 |
| 2 (C) | −44 | −27 | −81 | −54 | −58 | −38 | −91 | −68 | −47 | −27 | −82 | −55 |
| 3 (C) | −41 | −24 | −74 | −51 | −56 | −36 | −89 | −67 | −45 | −26 | −78 | −53 |
| 4 (C) | −37 | −22 | −69 | −47 | −49 | −33 | −80 | −62 | −44 | −25 | −72 | −49 |
| 5 (I) | −32 | −20 | −60 | −41 | −43 | −30 | −71 | −57 | −41 | −24 | −66 | −44 |
| 6 (I) | −33 | −20 | −60 | −40 | −43 | −31 | −70 | −58 | −41 | −23 | −65 | −45 |
| 7 (I) | −31 | −19 | −58 | −40 | −40 | −29 | −66 | −55 | −39 | −22 | −62 | −41 |
| 8 (I) | −28 | −18 | −53 | −35 | −37 | −27 | −61 | −52 | −37 | −20 | −58 | −37 |
| 9 (I) | −29 | −18 | −52 | −35 | −36 | −27 | −62 | −52 | −36 | −21 | −58 | −36 |
| 10 (I) | −33 | −21 | −61 | −40 | −42 | −30 | −72 | −58 | −42 | −24 | −66 | −45 |
| 11 (I) | −30 | −20 | −58 | −39 | −39 | −28 | −67 | −54 | −38 | −22 | −61 | −40 |
| 12 (I) | −32 | −20 | −57 | −41 | −40 | −29 | −67 | −55 | −38 | −23 | −62 | −40 |

(C = comparison; I = invention)

We claim:

1. A color photographic silver halide material which comprises at least one photosensitive silver halide emulsion layer and optionally a non-photosensitive layer, which is arranged close to the light source than the photosensitive silver halide emulsion layer, wherein at least one of said photosensitive layers or non-photosensitive layers contains a $TiO_2$ pigment having a primary particle diameter of 1 to 100 nm and at least one of said photosensitive layers or non-photosensitive layers contains at least one compound of the formulae (I) or (II)

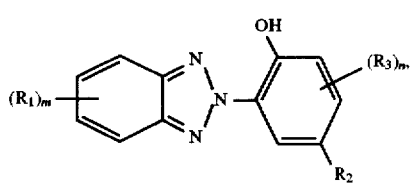
(I)

in which $R_1$ and $R_3$ independently of one another are halogen, alkyl, alkoxy, aryloxy, alkylthio, arylthio, acyloxy, acylamino or acyl;

$R_2$ means alkyl or acyl and m and n independently of one another are 0, 1 or 2 and two or more residues $R_1$ and $R_3$ are identical or different.

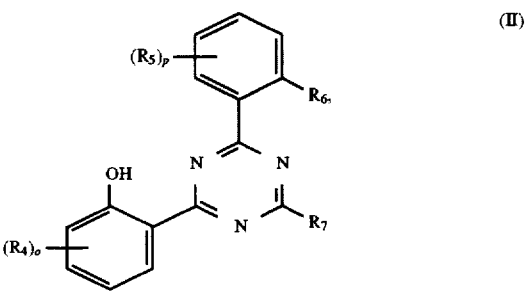
(II)

in which $R_4$ and $R_5$ independently of one another are H, halogen, hydroxy, mercapto, alkyl, aryl, alkoxy, aryloxy, acyloxy, alkylthio, arylthio, $-NR_8-R_9$ alkoxycarbonyl, carbamoyl or sulphamoyl;

$R_6$ means H, hydroxy, halogen or alkyl;

$R_7$ means alkyl, alkoxy, alkylthio, aryloxy, arylthio or a residue of the formula

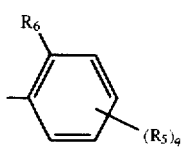

$R_8$ means H, alkyl or aryl;

$R_9$ means H, alkyl, aryl, acyl, alkoxycarbonyl, carbamoyl, sulphamoyl or sulphonyl;

o, p and q are identical or different and are 1, 2, 3 or 4, and in which two or more residues $R_4$, $R_5$ and $R_6$ are identical or different.

2. The color photographic material according to claim 1, wherein the compound of the formula II is of the formula III

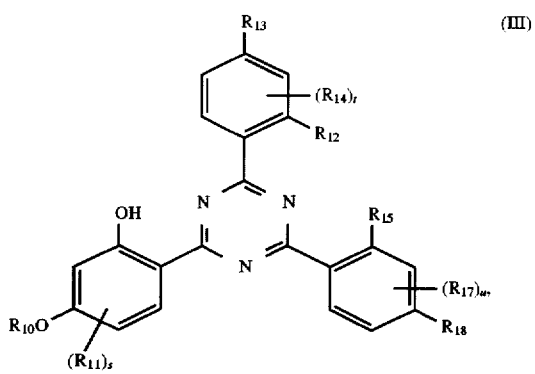

in which $R_{10}$ means H, alkyl, aryl or acyl;

$R_{11}$, $R_{14}$ and $R_{17}$ independently of one another are halogen, alkyl, aryl, alkoxy, aryloxy, acyloxy, alkylthio, arylthio or acylamino;

$R_{12}$, $R_{13}$, $R_{15}$ and $R_{16}$ independently of one another are H, —OH or $R_{11}$;

s, t, and u independently of one another are 0, 1 or 2.

3. The color photographic material according to claim 1, wherein the $TiO_2$ pigment is used in a total quantity of 5 to 3000 mg/m$^2$ and the compounds of the formulae (I) and (II) are used in a total quantity of 10 to 2000 mg/m$^2$.

4. The color photographic material according to claim 1, wherein the $TiO_2$ pigment has an $Fe_2O_3$ content of up to 20 wt. %, relative to the sum of $TiO_2$ and $Fe_2O_3$.

5. The color photographic material according to claim 1, wherein the $TiO_2$ pigment is coated on the surface with $SiO_2$ or $Al_2O_3$.

6. The color photographic material according to claim 1, wherein $R_1$ is Cl, m is 0 or 1, $R_3$ is alkyl and n is 1.

7. The color photographic material according to claim 1, wherein compound of the formula II is present and the compound is of the formula IV

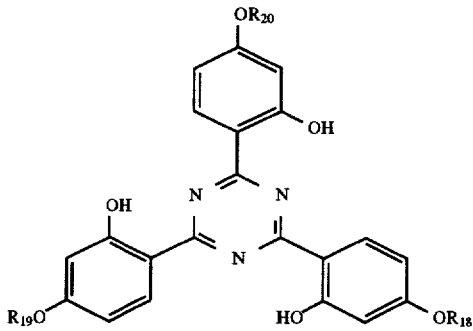

a) $R_{18} = R_{19} = R_{20} =$ —CH$_2$—CH(OH)—CH$_2$—O—C$_8$H$_{17}$-i, b) $R_{18} = R_{19} = R_{20} =$ —CH$_2$—CH(OH)—C$_6$H$_{13}$, c) $R_{18} = R_{19} =$ —C$_4$H$_9$-s, $R_{20} =$ —C$_{13}$H$_{23}$-i, d) $R_{18} =$ —CH$_2$—CH(OH)—CH$_2$—O—C$_4$H$_9$-s,

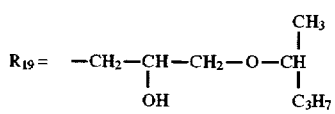

$R_{20} = R_{18}$ or $R_{19}$ e) $R_{18} =$ —CH$_2$—CH$_2$—O—CH$_2$—CH$_2$—O—C$_4$H$_9$, $R_{19} = R_{20} =$ —CH$_2$—CO$_2$—C$_8$H$_{17}$-i, or

-continued

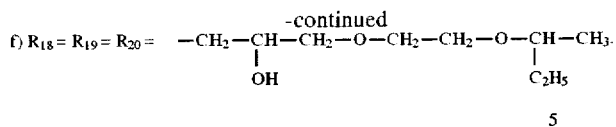

8. The color photographic material according to claim 1, wherein compound of the formula II is present and the compound is of the formula V

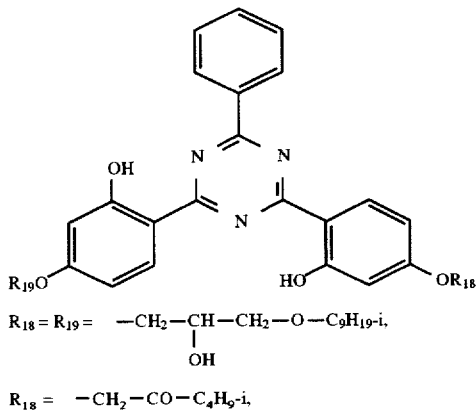

(V)

$R_{18} = R_{19} = -CH_2-CH-CH_2-O-C_9H_{19}\text{-i}$,
                |
                OH $R_{18} = -CH_2-CO-C_4H_9\text{-i}$,

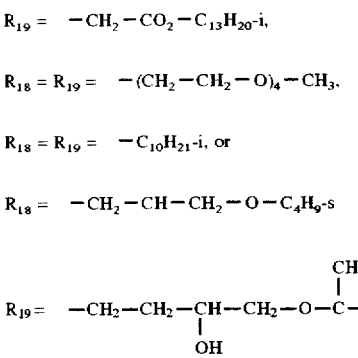

-continued $R_{19} = -CH_2-CO_2-C_{13}H_{20}\text{-i}$, $R_{18} = R_{19} = -(CH_2-CH_2-O)_4-CH_3$, $R_{18} = R_{19} = -C_{10}H_{21}\text{-i}$, or $R_{18} = -CH_2-CH-CH_2-O-C_4H_9\text{-s}$ 9. The color photographic material according to claim 1, wherein compound of the formula II is present and is selected from the group consisting of

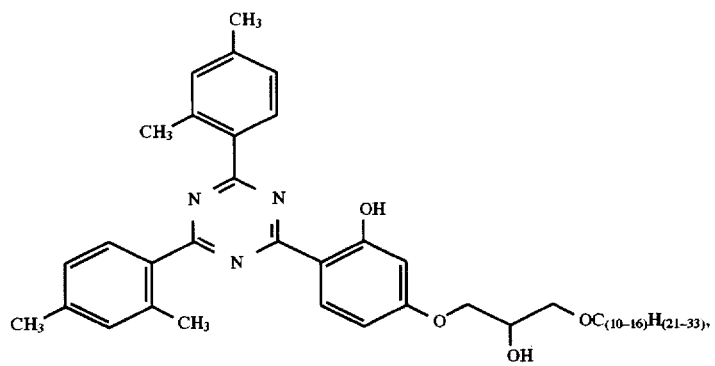

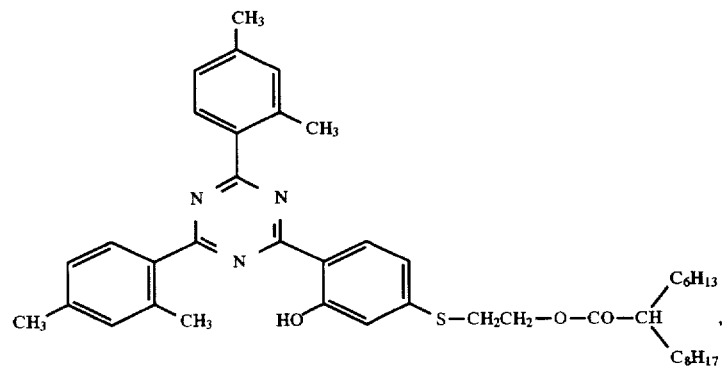

-continued
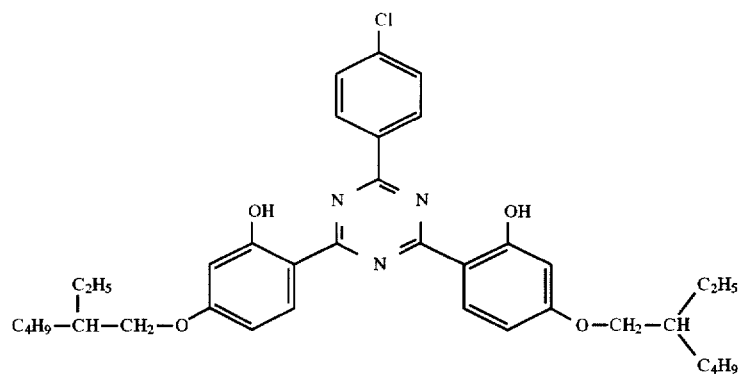
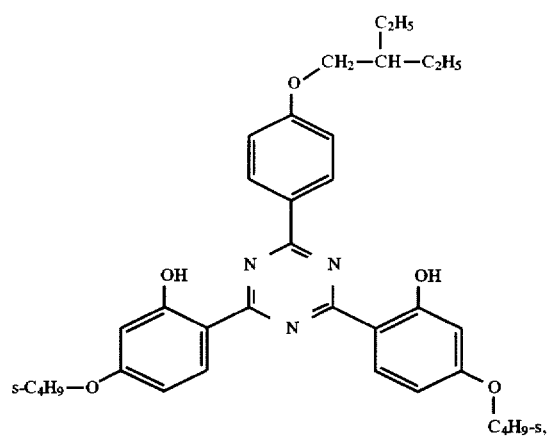
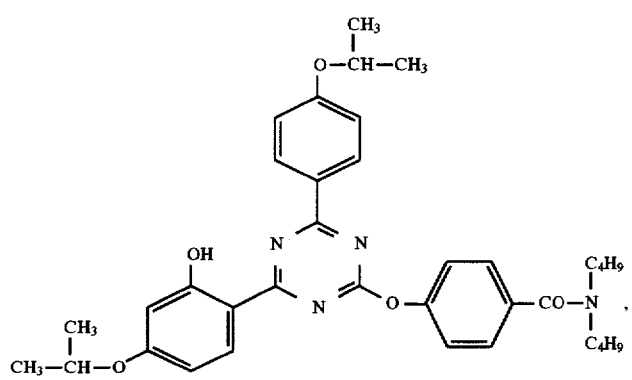
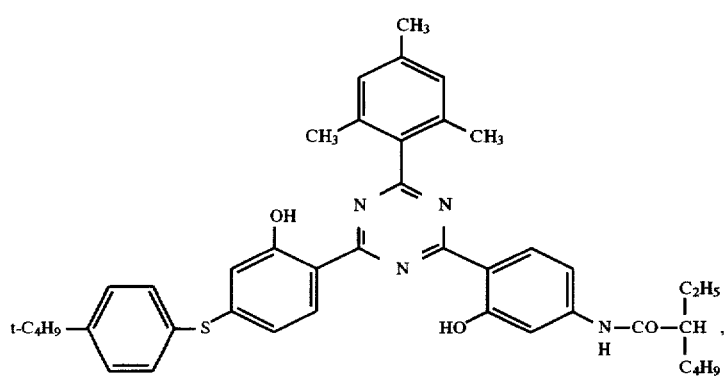

-continued
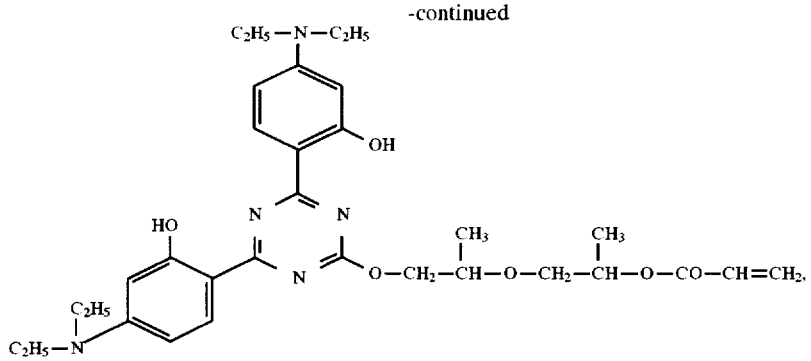
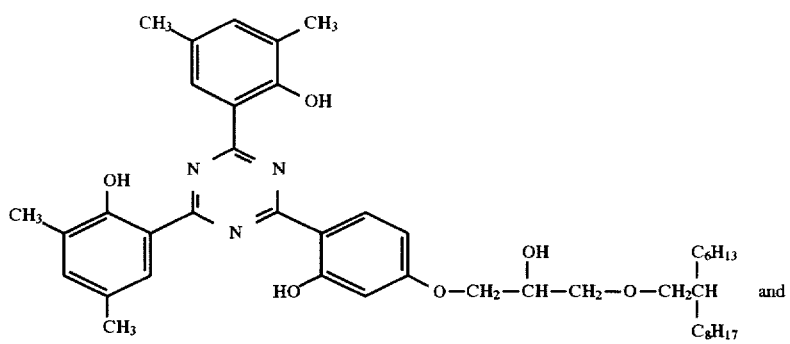 and
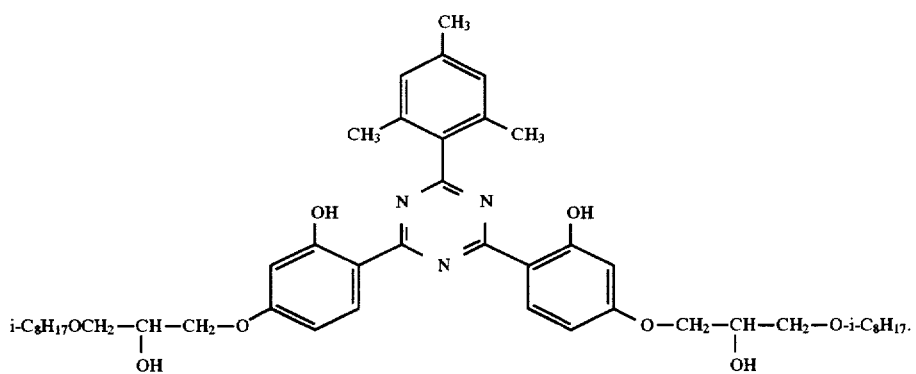
* * * * *